US006844482B2

(12) United States Patent
Eliasson

(10) Patent No.: US 6,844,482 B2
(45) Date of Patent: Jan. 18, 2005

(54) ABSORBENT ARTICLE WITH IMPROVED LIQUID ACQUISITION CAPACITY

(75) Inventor: Malin Eliasson, Molndal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/605,955

(22) Filed: Nov. 10, 2003

(65) Prior Publication Data

US 2004/0111074 A1 Jun. 10, 2004

Related U.S. Application Data

(60) Provisional application No. 60/425,722, filed on Nov. 13, 2002.

(51) Int. Cl.[7] ..................... A61F 13/539; A61F 13/472; A61F 13/15
(52) U.S. Cl. .................... 604/378; 604/385.01; 604/367
(58) Field of Search ................................. 604/378, 367, 604/385.101, 385.16, 385.201, 385.01, 385.17

(56) References Cited

U.S. PATENT DOCUMENTS

| 4,637,859 | A | * | 1/1987 | Trokhan ..................... 162/109 |
| 5,342,337 | A | | 8/1994 | Runeman et al. |
| 5,382,245 | A | * | 1/1995 | Thompson et al. ......... 604/367 |
| 5,545,156 | A | * | 8/1996 | DiPalma et al. ....... 604/385.23 |
| 5,591,148 | A | * | 1/1997 | McFall et al. .............. 604/378 |

FOREIGN PATENT DOCUMENTS

| WO | 94/10956 | 5/1994 |
| WO | 00/19955 | 4/2000 |
| WO | 01/24755 | 4/2001 |
| WO | 01/56625 | 8/2001 |
| WO | WO 0156625 A2 * | 8/2001 ........... A61L/15/00 |

OTHER PUBLICATIONS

Copy of International Search Report issued in a corresponding application.

* cited by examiner

Primary Examiner—John J. Calvert
Assistant Examiner—Ginger T Chapman
(74) Attorney, Agent, or Firm—Burns, Doane, Swecker & Mathis, L.L.P.

(57) ABSTRACT

An absorbent article having edge portions including two end edge portions and two side edge portions, and also a primary liquid reception area located in the longitudinal direction between the end edge portions and in the transverse direction between the side edge portions, an upper surface, and a lower surface, the upper surface being liquid-permeable at least within the primary liquid reception area, the article also including an absorption body with a liquid distribution layer. The absorption body includes an upper layer and a lower layer, the upper layer having at least two separate parts, of which a first part is arranged in the primary liquid reception area and a second part is arranged in an edge portion of the article, and the liquid distribution layer is arranged above both the upper layer and the lower layer in the liquid reception area and between the upper layer and the lower layer in the edge portion, and the liquid distribution layer has lower density than both the upper layer and the lower layer.

11 Claims, 4 Drawing Sheets

ABSORBENT ARTICLE WITH IMPROVED LIQUID ACQUISITION CAPACITY

CROSS REFERENCE TO RELATED APPLICATIONS

This application claims the benefit under 35 U.S.C. § 119(e) of U.S. provisional application 60/425,722 filed on Nov. 13, 2002, the entire content of which is incorporated by reference.

BACKGROUND OF INVENTION

1. Technical Field

The invention relates to an absorbent article, such as a diaper, an incontinence pad, a sanitary towel or the like, having an upper surface, which is intended to face a wearer during use, and a lower surface, which is intended to face away from the wearer during use, the upper surface being liquid-permeable at least within a primary liquid reception area, and an absorption body with a liquid distribution layer.

2. Related Art

One problem associated with absorbent articles intended for absorbing fluid bodily discharges, such as urine, menstrual fluid and runny motions, is that the penetration of the liquid into and the absorption of the liquid by the article do not take place sufficiently rapidly. In particular when urination takes place, and relatively large amounts of liquid are discharged in a short time and meet the article at high pressure, it is not an uncommon occurrence for liquid which is not taken up by the article to flow out over its surface instead and cause leakage. Another disadvantage of poor liquid acquisition capacity in an absorbent article is that the liquid is spread over the surface and causes the latter to become wet, which feels unpleasant against the skin of the wearer. This problem is especially marked in the case of highly viscous liquids, such as menstrual blood and loose motions. In addition to the fact that a wet surface can feel sticky and uncomfortable, there is of course also a risk of chafing and other irritation of the skin of the wearer.

U.S. Pat. No. 5,382,245 describes an absorbent article where a transport layer transfers liquid to a liquid storage layer. The transport layer preferably consists of fibres with superficial capillaries, and the liquid transport is therefore dependent on capillary forces. Such liquid transport is slow, and the article described in U.S. Pat. No. 5,382,245 is therefore not suitable for absorption of large amounts of bodily fluid or for minimizing wetting on the surface of an absorbent article.

A need therefore remains for an absorbent article with the capacity rapidly to acquire and absorb bodily fluid. There is also a need for an absorbent article which spreads the liquid in the article with minimum wetting of the surface of the article, so that the surface is kept as dry as possible during use.

SUMMARY OF INVENTION

An absorbent article has been produced which essentially eliminates the problems of previously known such products.

The absorbent article according to embodiments of the invention is characterized mainly in that the absorption body comprises an upper layer and a lower layer, the upper layer consisting of at least two separate parts, of which a first part is arranged in the primary liquid reception area and a second part is arranged in an edge portion of the article, and also in that a liquid distribution layer is arranged above both the upper layer and the lower layer in a liquid reception area and also between the upper layer and the lower layer in the edge portion, and also in that the liquid distribution layer has lower density than the upper layer and the lower layer.

By bending the liquid distribution layer around parts of the upper absorption layer, a number of favourable effects are achieved. The curvature of the liquid distribution layer results in the upper surface of the layer being stretched within the primary liquid reception area, owing to which the pore structure is opened up and liquid inflow into the layer is facilitated. Moreover, a pore size gradient is created in the layer, with larger pores at the upper surface where liquid first meets the layer and pores gradually decreasing in size in the direction towards the lower surface of the article. This means that liquid meeting the liquid distribution layer is conducted rapidly into it and can then be conveyed on to the surrounding absorption layers. Furthermore, by virtue of the liquid distribution layer being partly exposed to liquid reception and partly located between two absorption layers, the arrangement results in it being possible for the article to receive and distribute liquid into the absorption body in an optimum manner.

According to one embodiment of the invention, the liquid distribution layer is arranged between the upper absorption layer and the lower absorption layer at least in one end edge portion of the article and advantageously in both the end edge portions. In such an embodiment, liquid is conducted away from the primary liquid reception area to the end portions of the absorbent article.

It is also possible to arrange the liquid distribution layer between the upper absorption layer and the lower absorption layer at least in the side edge portions.

Materials which can be used in a liquid distribution layer according to the invention are, for example, fibrous waddings, superabsorbent foamed materials, or other spacing materials of lower density than the material in the absorption layers. It has been found to be especially advantageous to use the type of superabsorbent wadding described in WO 01/56625. Such a wadding material with acrylic acid polymerized in situ in the fibrous structure provides an open structure even after wetting. The material is well-suited for compression and has a good capacity for retaining the compression, which affords an opportunity for producing thin absorbent articles.

The upper absorption layer and the lower absorption layer preferably comprise a mixture of cellulose fluff pulp and superabsorbent material. Absorption layers made of only cellulose fluff pulp can also be used. The absorption material described in WO 94/10956 is such a material. This material is a dry-formed fibrous layer of high density which is used directly, without prior defibration. The fibrous material described in WO 94/10956 has very good absorption capacity. Other absorbent fibrous materials, such as rayon, peat, cotton etc., can also be used, individually or in combination, as can absorbent foamed materials. The absorption layers can moreover comprise non-absorbent reinforcing fibres, binding fibres or the like.

According to embodiments of the invention, it is furthermore possible for the liquid distribution layer, the upper absorption layer and the lower absorption layer to include or consist of the same type of material. In order that liquid transfer will take place from the liquid distribution layer to the surrounding absorption layers, the liquid distribution layer preferably has a lower density than the absorption layers.

In order to improve and control the liquid distribution in the article, the liquid distribution layer can be provided with compressions within an area which is located between the upper absorption layer and the lower absorption layer. Such compressions provide a compacted fibrous structure with small capillaries which conduct liquid. The compressions moreover form impressed channels or cavities in which liquid can run or be collected temporarily.

According to one embodiment of the invention, the absorption body is enclosed in a covering, the covering comprising a liquid-permeable portion which extends at least over the primary liquid reception area. Such a covering usually comprises a barrier layer for liquid, which is arranged on the lower surface, and a liquid-permeable covering layer, which is arranged on the upper surface. The article can moreover be provided with liquid-blocking material on the upper surface. Such a barrier material for liquid is then arranged over the edge portions on the upper surface. The edge barriers can be applied along the side edges of the article, along the end edges, or around the entire periphery of the article. By arranging liquid-blocking material on the upper surface, liquid which has been absorbed in the upper absorption layer is prevented from escaping back towards the body of the wearer. The barrier material for liquid on the upper surface of the article can also serve as a spacing layer and cohesion layer for the absorption material in the upper absorption layer in those embodiments where there is no liquid-permeable covering layer. In such embodiments, the liquid-distribution layer also constitutes a liquid reception layer and is directly exposed to the wearer. It is then preferable for the liquid distribution layer to have sufficient cohesion capacity of its own so as not to break or release fibres or particles during use of the article. Examples of materials with a good cohesion capacity are bound fibrous materials and foamed materials.

BRIEF DESCRIPTION OF DRAWINGS

The invention will be described in greater detail below with reference to the figures shown in the accompanying drawings, in which.

DETAILED DESCRIPTION

Figure 1:
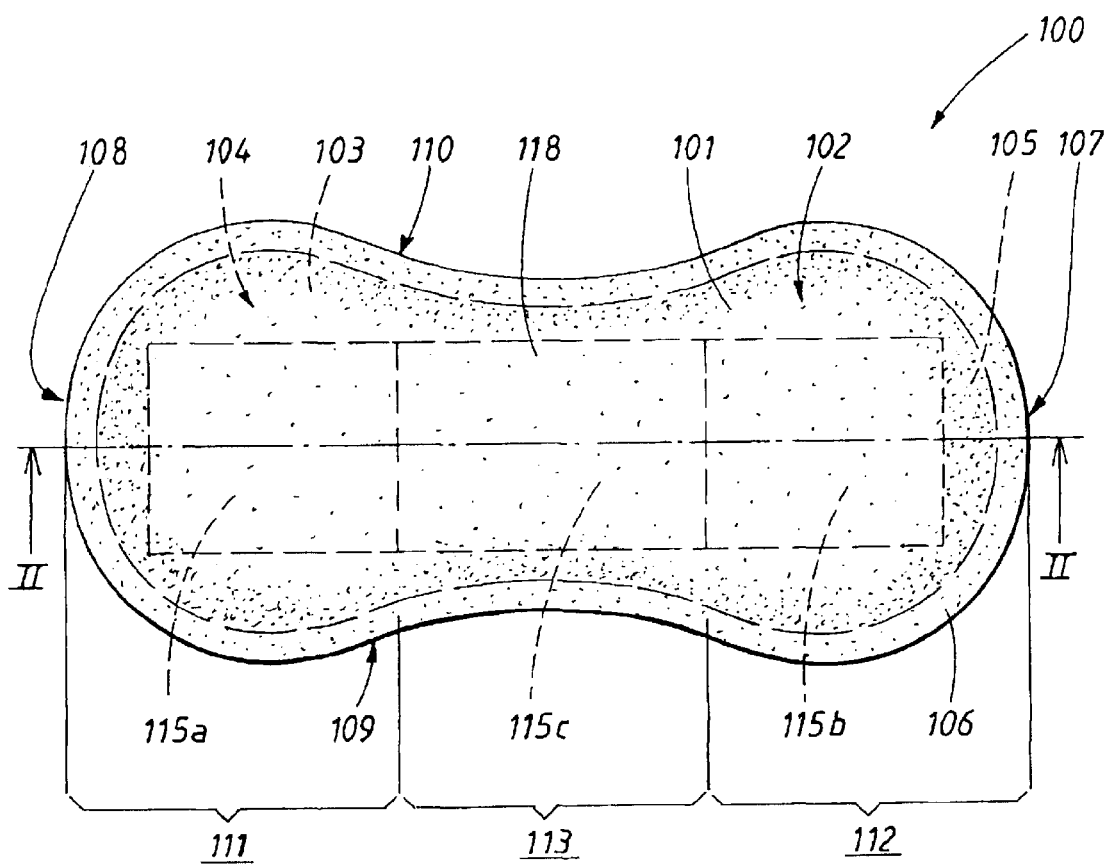
FIG. 1 shows a plan view of an incontinence pad according to a first embodiment of the invention.

The incontinence pad 100 shown in FIG. 1 comprises a liquid-permeable covering layer 101, which is arranged on the upper surface 102 of the incontinence pad, which is the surface intended to face the wearer during use, a liquid-impermeable covering layer 103, which is arranged on the lower surface 104 of the incontinence pad, which is the surface intended to face away from the wearer during use, and an absorption body 105 enclosed between the covering layers 101, 103. The two covering layers are interconnected by an edge join 106 which runs along the entire periphery of the absorption body 105. Such an edge join 106 can be brought about by, for example, gluing or welding, but mechanical joining methods such as needling and stamping can also be used.

The liquid-permeable covering layer 101 can be any material suitable for the purpose. Common liquid-permeable covering materials are various types of non-absorbent non-woven materials made of hydrophobic fibres which have been treated with surfactants in order to bring about liquid-permeability, perforated surfactant-treated plastic films, net or the like, and also open-cell foamed materials. Liquid-permeable laminates and other combinations of liquid-permeable covering materials are also suitable.

A thin flexible plastic film is usually used as the liquid-impermeable covering layer 103, but it is also known to use impermeable foamed materials, plastic shells with a greater or lesser degree of hardness, hydrophobic, impermeable non-woven materials or the like. It is often an advantage if the liquid-impermeable covering layer is breathable and therefore permits the passage of air and water vapour. In some cases, when the anticipated amount of liquid to be discharged into the pad is very small, the liquid-impermeable covering layer can be omitted altogether. Examples of absorbent articles where the liquid-impermeable covering layer can be omitted are panty liners and pads for people with drip incontinence. Alternatively, use can be made of a barrier layer which is not completely liquid-impermeable but which nevertheless resists liquid penetration.

The incontinence pad 100 has an hourglass shape with rounded end edges 107, 108 extending generally in the transverse direction of the incontinence pad and inwardly curved side edges 109, 110 extending generally in the longitudinal direction of the incontinence pad. The incontinence pad is furthermore designed with wider end edge portions 111, 112 and a narrower crotch portion 113 arranged between the end edge portions.

A fastener 114 in the form of a coating of glue is arranged on the liquid-impermeable covering layer 103. The fastener is intended to be used for fixing the incontinence pad 100 inside the pants of a wearer. In the example shown, the glue is arranged in the form of a full coating on the underside of the incontinence pad, but it is of course possible to use other forms of glue coating, such as strips, spots etc. During storage and transport of the incontinence pad, the glue coating is usually covered by a removable protective layer. Such protective layers generally are release-agent-treated paper strips. The invention is not limited to adhesive fasteners, but friction coatings and mechanical fixing arrangements such as hook and loop surfaces, press studs, clips etc. can also be used. Absorbent articles of the type concerned here may also be provided with fastening flaps. Such flaps are arranged at the side edges of the article and, for use, are folded around the leg edges on the pants of the wearer and fixed on the outside of the pants. The side flaps serve the dual purpose of constituting fixing means for the article and protecting the pants of the wearer against soiling.

The absorption body 105 has the same shape as the incontinence pad 100 as a whole and can therefore be divided in the same way into two end edge portions 111, 112 and a crotch portion 113.

The absorption body furthermore comprises an upper absorption layer 115, a lower absorption layer 116 and a liquid distribution layer 117. The upper absorption layer 115 is arranged next to the liquid-permeable covering layer 102, while the lower absorption layer 116 is arranged next to the liquid-impermeable covering layer 103. The upper absorption layer 115 has a rectangular shape and consists of three separate parts 115a, 115b, 115c, an end part 115a, 115b being arranged in each end edge portion 111, 112 of the incontinence pad 100, and a central part 115c being arranged in the crotch portion 113 of the incontinence pad. The lower absorption layer 116 and the liquid distribution layer 117 have the same shape as the absorption body 105 as a whole.

The two absorption layers 115, 116 can be any type of absorption material. A common absorption material is cellulose fluff pulp, with or without superabsorbents mixed in. Superabsorbents are polymers which can take up and absorb liquid corresponding to several times their own weight while forming a water-containing gel. The absorption layers can include the same material or of different materials. The liquid distribution layer 117 is a material which has the capacity to receive and transport liquid both in the plane (the X/Y directions) and in its thickness direction (the Z direction). Liquid distribution materials which can be used are various types of bonded fibrous waddings. As mentioned previously, a particularly suitable material is the type of superabsorbent wadding described in WO 01/56625. The relationship between the absorption layers 115, 116 and the liquid distribution layer 117 is to be such that liquid is transported in the direction from the liquid distribution layer 117 to the absorption layers 115, 116. This means that the absorption layers should have higher density than the liquid distribution layer 117.

The liquid distribution layer 117 is arranged in the absorption body 105 in such a way that it is located between the upper absorption layer 115 and the lower absorption layer 116 in the end edge portions 111, 112 of the incontinence pad 100 and between the liquid-permeable covering layer 101 and the upper absorption layer 115 in the crotch portion 113 of the incontinence pad. The liquid distribution layer 117 is therefore arranged between the end parts 115a, 115b of the upper absorption layer 115 and the lower absorption layer 116 but between the central part 115c of the upper absorption layer and the liquid-permeable covering layer 101, above both absorption layers 115, 116.

In this way, liquid meeting the incontinence pad 100 within the crotch portion 113 will be taken up by the liquid distribution layer 117 as soon as the liquid has passed through the liquid-permeable covering layer 101. That part of the upper surface 102 of the incontinence pad which coincides with that portion of the liquid distribution layer 117 exposed to direct liquid reception thus constitutes the primary liquid reception area 118 of the incontinence pad.

By virtue of the fact that the liquid distribution layer 117 is bent around the parts 115a, b, c in the upper absorption layer 115, the liquid distribution layer 117 is stretched at the upper surface of the incontinence pad. In this way, the fibrous structure in the liquid distribution layer 117 is opened up, which means that it is easier for liquid to flow into the layer 117. The liquid is then transported in the liquid distribution layer in between the end parts 115a, 115b of the upper absorption layer and the lower absorption layer 116. The invention therefore makes it possible to take up and distribute liquid inside an absorbent structure. The liquid is absorbed from the liquid distribution layer 117 both upwards to the upper absorption layer 115 and downwards to the lower absorption layer 116. The limited primary liquid reception area 118 means that the wet surface which can come into contact with the skin of the wearer is minimized. It is also an advantage that the liquid is distributed and absorbed inside the absorption body, which means that large amounts of liquid can be taken up in the absorption body before it is so saturated that liquid escapes back up towards the upper surface of the incontinence pad.

As can be seen from FIG. 1, the liquid distribution layer 117 is slightly shorter and narrower than other parts of the absorption body. Such an embodiment is in many cases advantageous from the point of view of leakage, because it means that liquid is not transported all the way out to the edges of the absorbent article. The liquid distribution layer 117 can of course, within the scope of the invention, be even shorter than shown in FIG. 1. Another advantage of using a liquid distribution layer which is shorter and/or narrower than the absorption body in general is that a cost-saving is achieved in this way, especially as the material in the liquid distribution layer 117 is often of a more sophisticated and thus more expensive type than the other absorption material.

Figure 2:
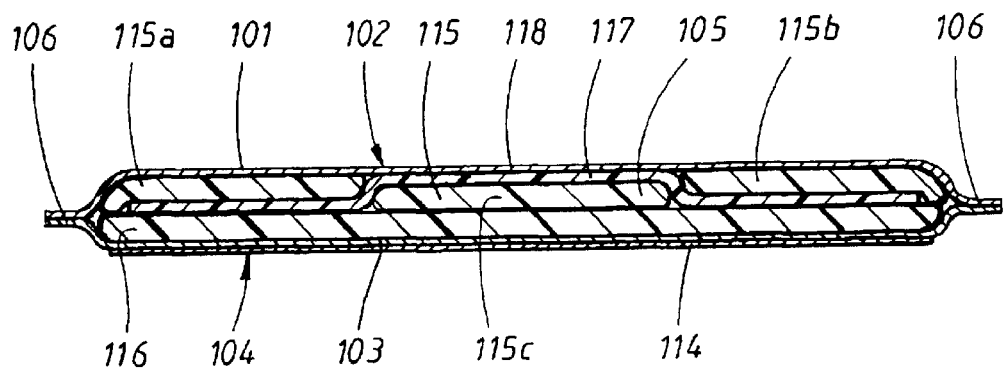
FIG. 2 shows a longitudinal section along the line II—II through the incontinence pad in FIG. 1.
Figure 3:
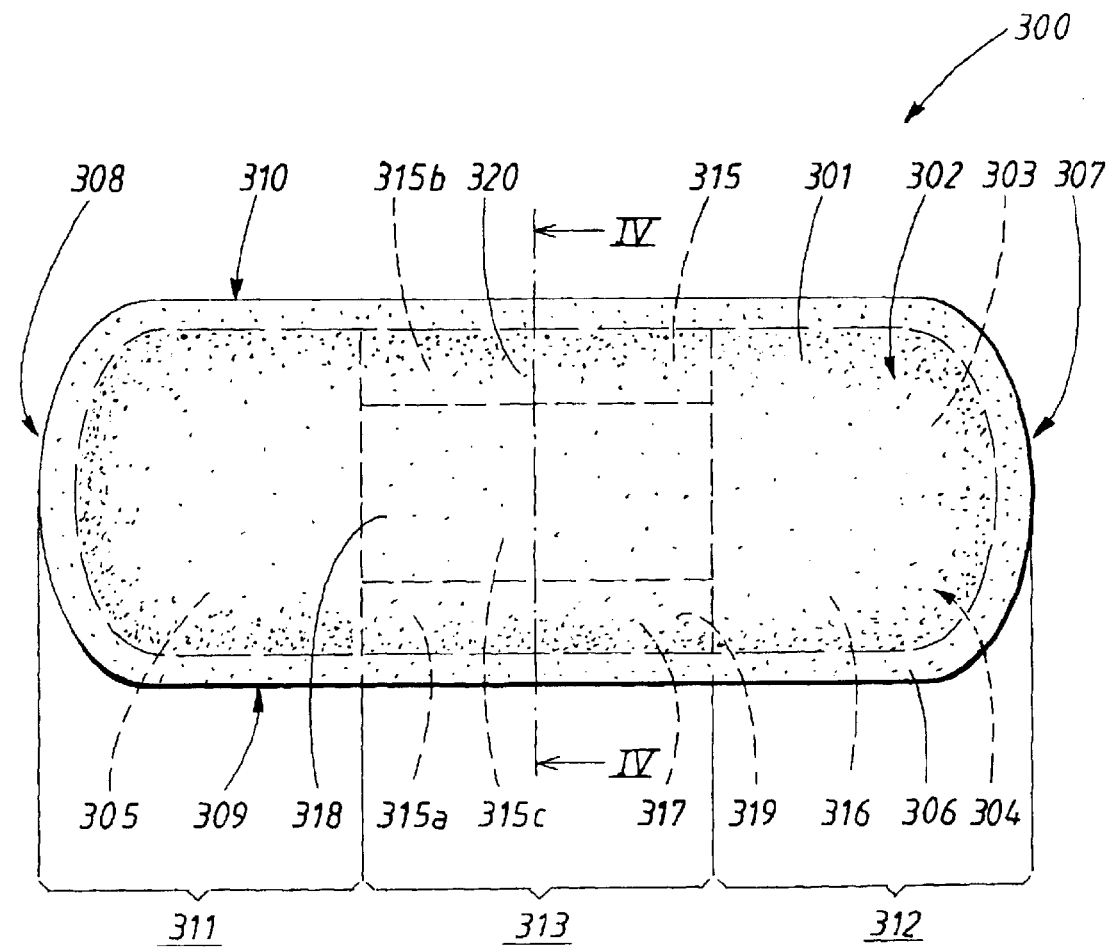
FIG. 3 shows a plan view of a sanitary towel according to a second embodiment of the invention.
Figure 4:
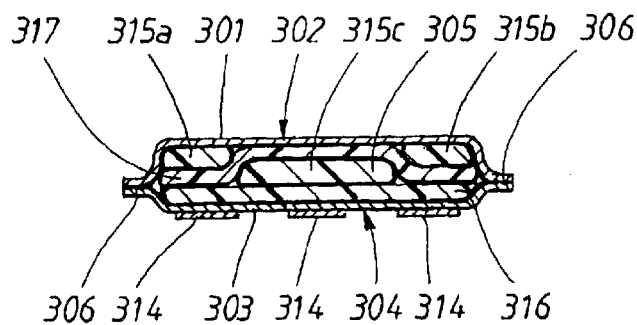
FIG. 4 shows a cross section through the sanitary towel in FIG. 3 along the line IV—IV.

FIGS. 3 and 4 show a sanitary towel 300 with in principle the same construction as the incontinence pad 100 in FIGS. 1 and 2. The sanitary towel 300 therefore comprises an absorption body 305 enclosed between a liquid-permeable covering layer 301, located on an upper surface 302 of the sanitary towel 300, and a liquid-impermeable covering layer 303 located on a lower surface 304 of the sanitary towel. The covering layers 301, 303 are interconnected in an edge join 306 which extends around the absorption body 305.

The sanitary towel 300 is generally rectangular and has transverse end edges 307, 308 and longitudinal side edges 309, 310. The sanitary towel is furthermore divided in the longitudinal direction into two end edge portions 311, 312 and a crotch portion 313 located centrally between the end edge portions. In the transverse direction, the crotch portion is divided into two side edge portions 319, 320 and a primary liquid reception area 318 which is located centrally between the side edge portions 319, 320.

Like the incontinence pad in FIGS. 1 and 2, the sanitary towel 300 is provided with a fastener 314. In the example shown, the fastener 314 includes three glue strands arranged on the liquid-impermeable covering layer 303 on the lower surface 304 of the sanitary towel.

The absorption body 305 comprises an upper absorption layer 315 consisting of three parts 315a, 315b and 315c. In this connection, two side edge parts 315a, 315b are arranged in the side edge portions 319, 320 of the sanitary towel 300, and a dogbone-shaped central part 315c is arranged between the side edge parts 315a, 315b and in the end edge portions 311, 312. The absorption body 305 furthermore comprises a lower absorption layer 316 with essentially the same shape and extent as the absorption body 305 and the sanitary towel as a whole. A rectangular liquid distribution layer 317 is arranged in the crotch portion 313 and is located between the liquid-permeable covering layer 301 and the upper absorption layer 315 within the primary liquid reception area 318 and between the upper absorption layer 315 and the lower absorption layer 316 within the side edge portions 319, 320. The liquid distribution layer 317 is therefore arranged above the narrower portion of the central part 315c of the upper absorption layer 315 and below the side edge parts 315a, 315b of the upper absorption layer.

Figure 5:
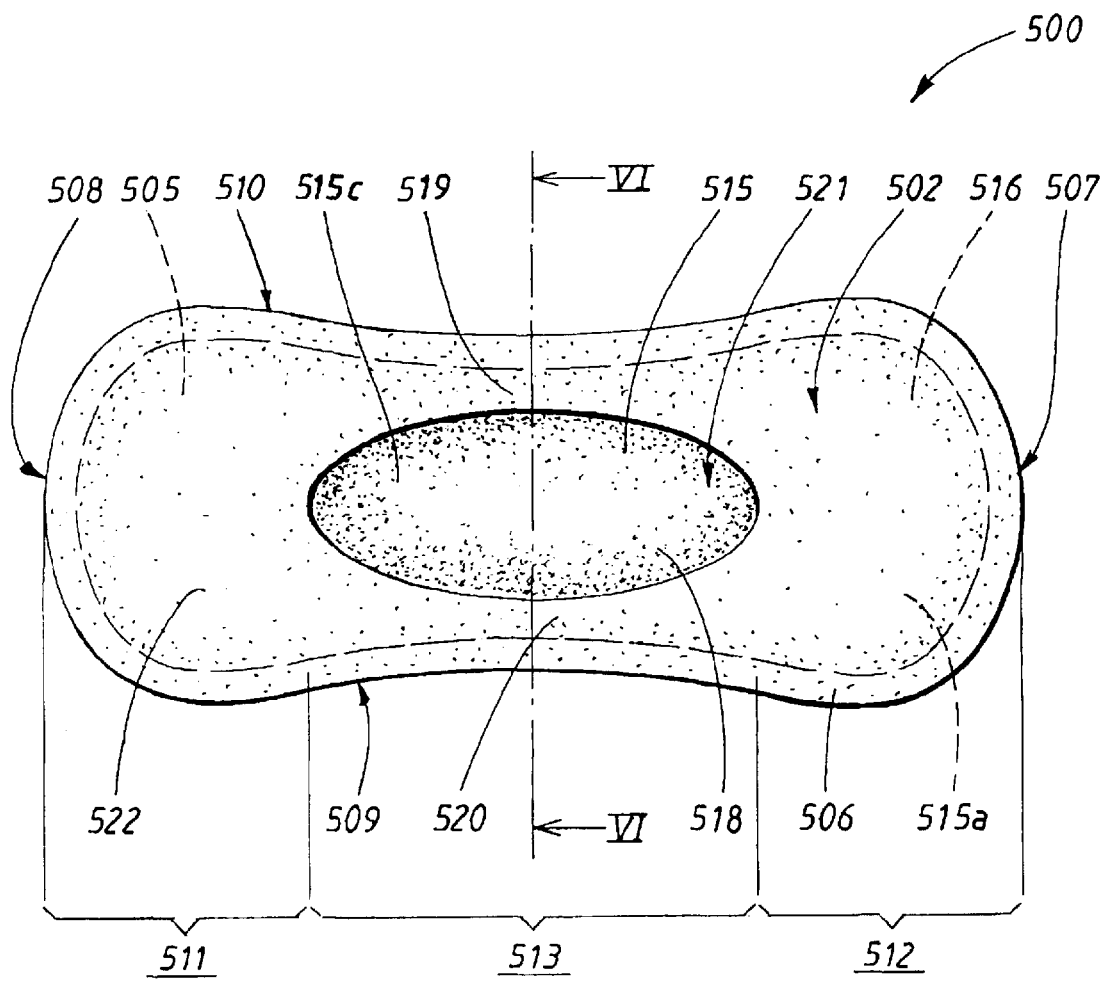
FIG. 5 shows a plan view of an incontinence pad according to a third embodiment of the invention.
Figure 6:
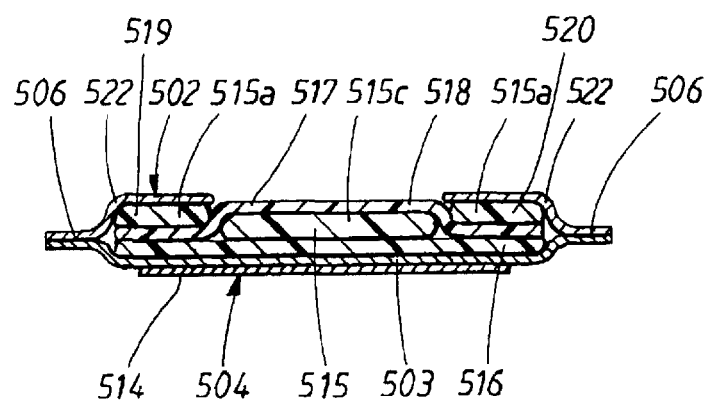
FIG. 6 shows a cross section along the line VI—VI through the incontinence pad in FIG. 5.

The incontinence pad 500 shown in FIGS. 5 and 6 has an hourglass shape with inwardly curved side edges 509, 510 and outwardly curved end edges 507, 508. The incontinence pad is furthermore shaped with wider end portions 511, 512 and a narrower crotch portion 513.

In contrast to the previously described absorbent articles, the incontinence pad 500 does not have a separate liquid-permeable covering layer on the upper surface 502. However, a liquid-impermeable covering layer 503 is arranged on the lower surface 504 of the incontinence pad and is provided with an adhesive fastener 514 in the same way as described above.

Like the previously described articles, the incontinence pad in FIGS. 5 and 6 comprises an absorption body with an upper and a lower absorbent layer 515, 516 and a liquid distribution layer 517. The upper absorbent layer 515 consists of two parts 515a, 515c, of which a central part of oval shape is located in the primary liquid reception area 518 of the incontinence pad and a surrounding part 515a extends over the end edge portions 511, 512 and side edge portions 519, 520 of the incontinence pad. In this connection, the surrounding part 515a has an opening 521 of the same shape and size as the oval central part 515c. The lower absorbent layer 516 and the liquid distribution layer 517 both have the same hourglass shape as the incontinence pad and the absorption body 505 as a whole.

The liquid distribution layer 517 is arranged above the central part 515c of the upper absorption layer 515 within the primary liquid reception area 518 and between the upper and lower absorption layers 515, 516 within the end edge portions 511, 512 and the side edge portions 519, 520. This means that the liquid distribution layer 517 is exposed through the opening 521 in the surrounding part 515a of the upper absorption layer 515. Liquid meeting the incontinence pad 500 can therefore flow directly into the liquid distribution layer 517.

In order to prevent liquid leaking out at the side edges 509, 510 of the incontinence pad 500 and in order to afford as dry a surface as possible against the skin of the wearer, an upper covering layer 522 is arranged over the surrounding part 515a of the upper absorption layer 515. The upper covering layer 522 therefore has, like the upper absorption layer 515, an opening 521, through which liquid can pass into the incontinence pad 500. The upper covering layer 522 is suitably a barrier layer for liquid, or at least a layer which resists liquid penetration or prevents re-wetting, that is to say absorbed liquid escaping from the incontinence pad 500 through the upper surface 502. Materials which can be used for the upper covering layer are hydrophobic non-woven materials, plastic film, non-woven/plastic film laminates, perforated plastic films etc. The upper covering layer 522 is joined together with the liquid-impermeable covering layer 503 in an edge join 506 around the entire periphery of the absorption body 505.

Figure 7:
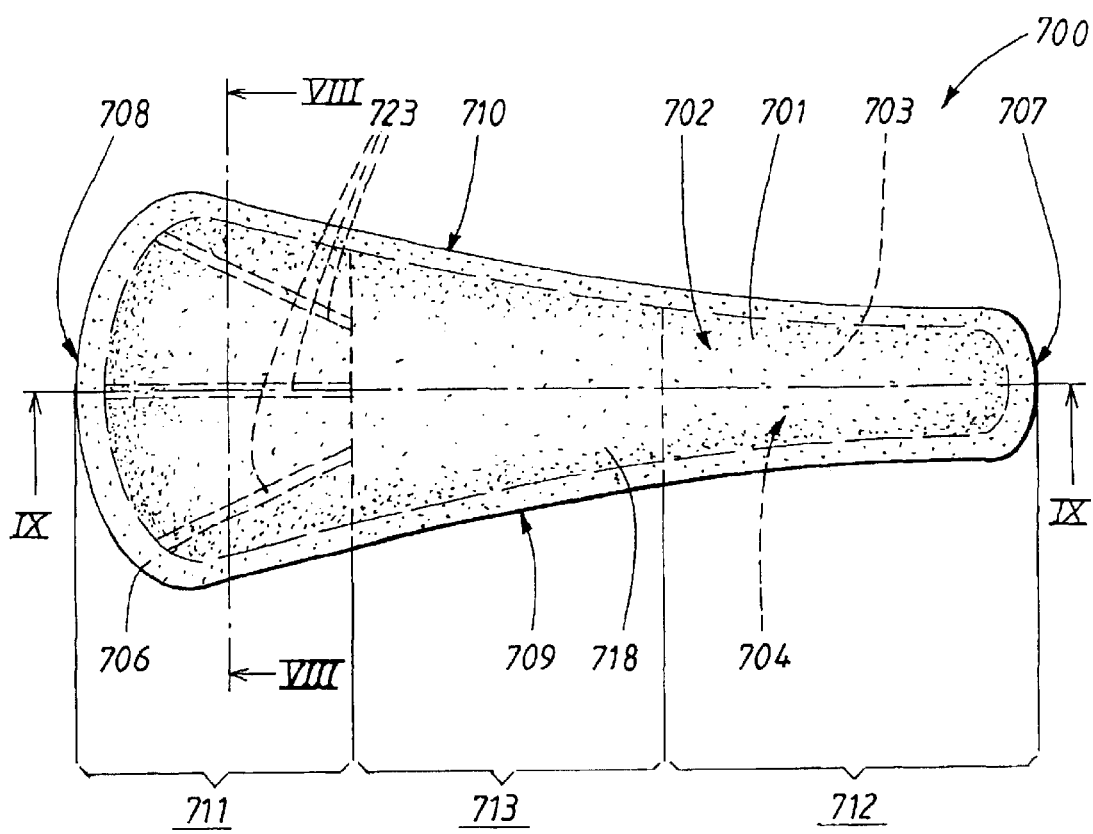
FIG. 7 shows a plan view of a sanitary towel according to a fourth embodiment of the invention.
Figure 8:
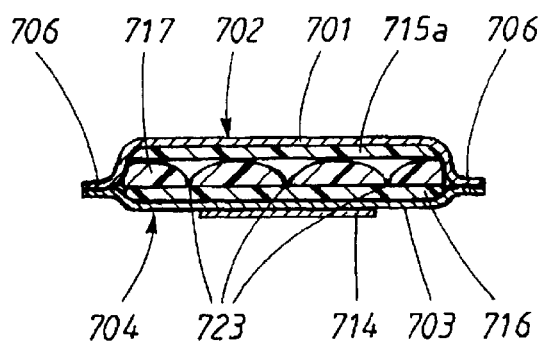
FIG. 8 shows a cross section along the line VIII—VIII through the sanitary towel in FIG. 7.
Figure 9:
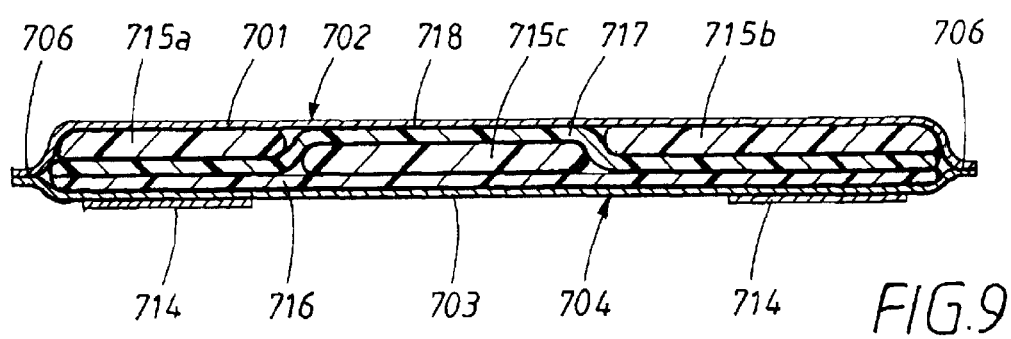
FIG. 9 shows a longitudinal section along the line IX—IX through the sanitary towel in FIG. 7.

FIGS. 7–9 show a sanitary towel 700 with a shape which is particularly suitable for use together with what are known as string panties, that is to say briefs with a very small rear portion. The sanitary towel 700 comprises a liquid-permeable covering layer 701 arranged on the upper surface 702, a liquid-impermeable covering layer 703 arranged on the lower surface 704 and an absorption body enclosed between the covering layers 701, 703. The covering layers 701, 703 are interconnected by an edge join 706 which runs around the absorption body.

The sanitary towel 700 has an essentially triangular shape with transverse end edges 707, 708, longitudinal side edges 709, 710 and a wide front end portion 711 which tapers via a crotch portion 713 towards a very narrow, virtually strip-shaped rear end portion 712.

The absorption body comprises an upper absorbent layer 715 and a lower absorbent layer 716 and a liquid distribution layer 717. The upper absorbent layer 715 consists of three parts 715a, 715b and 715c, of which a central part 715c is located in the primary liquid reception area 718 of the sanitary towel and a front end edge part 715a extends over the front end edge portion 711 of the sanitary towel and a rear end edge part 715b extends over the rear end edge portion 712 of the sanitary towel 700. The lower absorbent layer 716 and the liquid distribution layer 717 both have the same essentially triangular shape as the sanitary towel and the absorption body as a whole.

The liquid distribution layer 717 is arranged above the central part 715c of the upper absorption layer 715 within the primary liquid reception area 718 and between the upper and lower absorption layers 715, 716 within the end edge portions 711, 712.

In order to heighten the liquid-spreading capacity of the liquid distribution layer 717 and in order to guide the liquid-spreading towards the front end edge portion 711 of the sanitary towel, the front end edge portion of the liquid distribution layer 717 is provided with compression strips 723 which form channels in which liquid can run in between the absorption layers 715, 716. Liquid can also be actively transported in the compacted fibrous structure in the compression strips.

Like the previously described absorbent articles, the sanitary towel in FIGS. 7–9 is provided with a fastener 714. In FIG. 9, it can be seen that the fastener 714 includes two glue surfaces, one positioned in each end edge portion 711, 712, on the liquid-impermeable covering layer 703.

The invention is not to be regarded as being limited to the embodiments described here, but a number of further variants and modifications are conceivable within the scope of the patent claims below. In particular, the shape of the absorbent articles can be varied, as can the shape of the various component layers.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent article comprising a transverse direction and a longitudinal direction, two end edges extending in the transverse direction, two side edges extending in the longitudinal direction, edge portions comprising two end edge portions located at the end edges and two side edge portions located at the side edges, and also a primary liquid reception area located in the longitudinal direction between the end edge portions and in the transverse direction between the side edge portions, an upper surface, which is adapted to face a wearer during use, and a lower surface, which is adapted to face away from a wearer during use, the upper surface being liquid-permeable at least within the primary liquid reception area, the absorbent article also comprising an absorption body with a liquid distribution layer, the absorption body comprises an upper layer and a lower layer, the upper layer having at least two separate parts, of which a first part is arranged in the primary liquid reception area and a second part is arranged in at least one of the edge portions of the article, and the liquid distribution layer is arranged above both the upper layer and the lower layer in the liquid reception area and between the upper layer and the lower layer in the at least one edge portion, and the liquid distribution layer has lower density than both the upper layer and the lower layer.

2. The absorbent article according to claim 1, wherein the liquid distribution layer is arranged between the upper absorption layer and the lower absorption layer at least in one end edge portion of the article.

3. The absorbent article according to claim 2, wherein the liquid distribution layer is arranged between the upper absorption layer and the lower absorption layer in both the end edge portions.

4. The absorbent article according to claim 1, wherein the liquid distribution layer is arranged between the upper absorption layer and the lower absorption layer at least in the side edge portions.

5. The absorbent article according to claim 1, wherein the liquid distribution layer comprises a layer of superabsorbent wadding.

6. The absorbent article according to claim 1, wherein the liquid distribution layer, the upper absorption layer and the lower absorption layer comprise the same type of material.

7. The absorbent article according to claim 1, wherein the upper absorption layer and the lower absorption layer comprise a mixture of cellulose fluff pulp and superabsorbent material.

8. The absorbent article according to claim 1, wherein the liquid distribution layer has compressions within an area which is located between the upper absorption layer and the lower absorption layer.

9. The absorbent article according to claim 1, wherein the absorption body is enclosed in a covering, and the covering comprises a liquid-permeable portion which extends at least over the primary liquid reception area.

10. The absorbent article according to claim 9, wherein the covering comprises a liquid barrier layer, which is arranged on the lower surface.

11. The absorbent article according to claim 1, wherein a liquid barrier material is arranged over the edge portions on the upper surface.

* * * * *